United States Patent
Joensen et al.

(10) Patent No.: US 10,336,673 B2
(45) Date of Patent: *Jul. 2, 2019

(54) PROCESS FOR CONVERTING METHANOL TO HYDROCARBONS SUITABLE FOR USE AS GASOLINE OR BLENDSTOCK

(71) Applicant: HALDOR TOPSØE A/S, Kgs. Lyngby (DK)

(72) Inventors: Finn Joensen, Hørsholm (DK); Uffe Vie Mentzel, Vanløse (DK); Ian Menjon, Copenhagen Ø (DK)

(73) Assignee: HALDOR TOPSØE A/S, KGS. Lyngby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/544,670

(22) PCT Filed: Jan. 22, 2016

(86) PCT No.: PCT/EP2016/051367
§ 371 (c)(1),
(2) Date: Jul. 19, 2017

(87) PCT Pub. No.: WO2016/116612
PCT Pub. Date: Jul. 28, 2016

(65) Prior Publication Data
US 2018/0022673 A1   Jan. 25, 2018

(30) Foreign Application Priority Data

Jan. 22, 2015 (DK) .................................. 2015 70042

(51) Int. Cl.
| | | |
|---|---|---|
| C07C 1/20 | (2006.01) | |
| C07C 29/141 | (2006.01) | |
| B01J 29/40 | (2006.01) | |
| C10G 3/00 | (2006.01) | |
| C07C 9/08 | (2006.01) | |
| C07C 9/10 | (2006.01) | |
| C07C 31/04 | (2006.01) | |

(52) U.S. Cl.
CPC .......... *C07C 29/141* (2013.01); *B01J 29/405* (2013.01); *C07C 1/20* (2013.01); *C07C 9/08* (2013.01); *C07C 9/10* (2013.01); *C10G 3/42* (2013.01); *C10G 3/46* (2013.01); *C10G 3/49* (2013.01); *C10G 3/50* (2013.01); *C10G 3/54* (2013.01); *C07C 31/04* (2013.01); *C07C 2529/40* (2013.01); *C10G 2300/4081* (2013.01); *C10G 2300/805* (2013.01); *C10G 2400/02* (2013.01); *Y02P 20/52* (2015.11); *Y02P 30/20* (2015.11)

(58) Field of Classification Search
CPC ........ C07C 41/00; C07C 43/043; C07C 1/22; C07C 29/152; C07C 41/01; C10G 2400/02; C10G 3/45; C10G 3/49; C10G 50/00; C10G 3/42; C10G 3/44; C10G 3/46; C10G 3/50; C10G 3/54; C10G 45/64; C10G 47/16; B01J 2523/00; B01J 29/40; B01J 21/04; B01J 23/002
See application file for complete search history.

(56) References Cited

U.S. PATENT DOCUMENTS

| | | | |
|---|---|---|---|
| 3,948,758 | A | 4/1976 | Bonacci et al. |
| 4,523,046 | A | 6/1985 | Gould et al. |
| 4,543,435 | A | 9/1985 | Gould et al. |
| 4,684,757 | A | 8/1987 | Avidan et al. |
| 4,788,369 | A | 11/1988 | Marsh et al. |
| 4,835,329 | A | 5/1989 | Harandi et al. |
| 4,851,606 | A | 7/1989 | Ragonese et al. |
| 5,656,149 | A | 8/1997 | Zones et al. |
| 6,372,680 | B1 | 4/2002 | Wu et al. |
| 9,296,665 | B2 * | 3/2016 | Kortan .................. C07C 41/00 |
| 2008/0045403 | A1 | 2/2008 | Rollins et al. |
| 2014/0171691 | A1 | 6/2014 | Kortan et al. |

FOREIGN PATENT DOCUMENTS

EP    0 087 862 A1    9/1983

OTHER PUBLICATIONS

International Search Report (PCT/ISA/210) dated Apr. 25, 2016, by the European Patent Office as the International Searching Authority for International Application No. PCT/EP2016/051367.
Written Opinion (PCT/ISA/237) dated Apr. 25, 2016, by the European Patent Office as the International Searching Authority for International Application No. PCT/EP2016/051367.
Office Action dated Aug. 31, 2015, by the Danish Patent Office for Application No. PA 2015 70042.

* cited by examiner

*Primary Examiner* — Sharon Pregler
(74) *Attorney, Agent, or Firm* — Buchanan Ingersoll & Rooney P.C.

(57) ABSTRACT

The present application relates to a process for production of hydrocarbons comprising the steps of
   converting a feed stream comprising alcohols, ethers or mixtures hereof over a metal-containing zeolite based catalyst, active in dehydrogenation of hydrocarbons, in a conversion step thereby obtaining a conversion effluent,
   separating said effluent to obtain an aqueous process condensate stream, a liquid hydrocarbon stream and a gaseous stream,
   removing part of the hydrogen formed in the conversion step, and
recycling at least part of the gaseous and/or liquid hydrocarbon stream to the conversion step.

30 Claims, 4 Drawing Sheets

PROCESS FOR CONVERTING METHANOL TO HYDROCARBONS SUITABLE FOR USE AS GASOLINE OR BLENDSTOCK

The conversion of methanol (MeOH) and/or dimethyl ether (DME), into hydrocarbon fuels and chemicals is of significant industrial importance. Prominent examples comprise methanol-to-gasoline (MTG) and methanol-to-olefins (MTO) processes.

In general, any alcohol and ether may be converted into hydrocarbons by these processes, but methanol is the preferred feedstock, because it may be produced in large scale and with high efficiency from any carbon-containing resource, such as coal, biomass, waste and natural gas. Prior, to the conversion into hydrocarbons the methanol or alcohol feed may be converted, at least partially, into its ether analogue e.g. methanol to DME.

Similar processes have been disclosed for the conversion of alcohols into hydrocarbons, targeting different products such as aromatics.

The MTG process typically provides high-octane synthetic gasoline in excellent yields, close to about 90 percent by weight of the total amount of hydrocarbons produced and with typical octane numbers close to 90, expressed in terms of (R+M)/2 (R=Research Octane Number, M=Motor Octane Number). The synthetic gasoline typically contains substantial amounts of aromatics which contribute significantly to the octane number. Even higher octane numbers may be obtained by increasing the aromatics content, e.g. by increasing the pressure or temperature in the gasoline synthesis reactor or by reducing the space velocity. Changing synthesis conditions to improve aromatics selectivity, and thereby octane, however, imposes a penalty in terms of a reduced gasoline yield, because the formation of aromatics is inherently accompanied by increased selectivity to paraffins, in particular, propane and butanes which only to a limited extent may be added to the gasoline product slate due to their relatively high vapour pressures. In other words, the existing choice is between making a low-aromatics product in high yields or a high-aromatics product in low yields.

In a first aspect of the present invention is provided a process and plant for producing a hydrocarbon product with enhanced aromatics and/or C5+ selectivity (selectivity to hydrocarbons with carbon number 5 and higher) by decreasing the selectivity to light paraffins such as propane and butanes.

In a second aspect of the present invention is provided a process for the production of gasoline or gasoline blendstok with reduced formation of durene (1,2,4,5-tetramethylbenzene).

In a third aspect of the present invention is provided a process for the production of gasoline or gasoline blendstock with reduced formation of hydrocarbons with carbon number higher than 10

In a fourth aspect of the present invention is provided a process for the production of a highly aromatic gasoline blendstock.

These and other advantages are provided by a process for production of hydrocarbons comprising the steps of
converting a feed stream comprising alcohols, ethers or mixtures hereof over a metal-containing zeolite based catalyst, active in dehydrogenation of hydrocarbons, in a conversion step thereby obtaining a conversion effluent,
separating said effluent to obtain an aqueous process condensate stream, a liquid hydrocarbon stream and a gaseous stream,
removing part of the hydrogen formed in the conversion step, and
recycling at least part of the gaseous and/or liquid hydrocarbon stream to the conversion step.

I.e. according to the present invention there is provided a process for making a hydrocarbon product in which hydrogen produced in the conversion step is removed or partially removed from the synthesis loop, either by purging part of the gaseous recycle stream, hereinafter referred to as passive $H_2$ rejection, or by removing, partially or completely, $H_2$ from one or more recycle streams, hereinafter referred to as active $H_2$ rejection, in order to provide an at least partly $H_2$ depleted recycle. In the process e.g. methanol is converted over a preferably acidic zeolite based catalyst, combined with a metal or metal oxide component active in the dehydrogenation of hydrocarbons, into a conversion effluent comprising aromatics.

The conversion effluent is separated into a gaseous stream, an aqueous process condensate and a liquid hydrocarbon stream comprising a hydrocarbon product.

By the present process and plant wherein hydrogen is removed it is possible to increase the aromatics and/or C5+ selectivity by reducing the selectivity to light paraffins, such as propane and butanes.

The obtained hydrocarbon stream may be rich in aromatics, in which case the process hereinafter is referred to as a methanol-to-aromatics (MTA) process.

In the MTA conversion process methanol is converted into aromatics while dehydrogenation of hydrocarbons including one or more types of hydrocarbons, comprising naphthenes, paraffins and isoparaffins, into olefins and/or aromatics is taking place.

The MTA conversion process may preferably be carried out at a pressure 5-60 bar, preferably 10-40 bar, temperature 300-500° C., preferably 330-480° C. and/or weight hourly space velocities (kg alcohol and/or ether feed per kg of catalyst per hour) between 0.1 and 10 preferably 0.3-3.

The MTA process may provide a product particularly suited as feedstock for downstream aromatics processing, e.g. for making para-xylene.

The MTA process may also provide a hydrocarbon product rich in aromatics, which product may be applied as a gasoline product in form of reformate blendstock.

The obtained hydrocarbon stream from the present process may comprise raw gasoline, in which case the process hereinafter is referred to as a methanol-to-gasoline (MTG) process.

In the MTG conversion process methanol is converted into a raw gasoline comprising aromatics, naphthenes, paraffins and isoparaffins and olefins while dehydrogenation of hydrocarbons including one or more types of hydrocarbons, comprising naphthenes, paraffins and isoparaffins, into olefins and/or aromatics is taking place.

The MTG conversion process may preferably be carried out at a pressure 5-60 bar, preferably 10-40 bar, temperature 300-500° C., preferably 300-430° C. and weight hourly space velocities (kg alcohol and/or ether feed per kg of catalyst per hour) between 0.1 and 10 preferably 0.5-3.

In other words, the overall traditional MTA/MTG reaction, may be formulated as a mere dehydration, of methanol, forming hydrocarbons and water:

$$CH_3OH \rightarrow CH_2 + H_2O,$$

where $CH_2$ denotes the sum formula of the entire hydrocarbon product. Thus, the overall molar hydrogen-to-carbon ratio of the entire hydrocarbon product is two: H/C=2. Some of the product hydrocarbons, aromatics, have H/C ratios below 2, paraffins and isoparaffins have H/C ratios above 2, whereas olefins and naphthenes both have H/C equal to 2.

As opposed to traditional MTA/MTG this invention provides a hydrocarbon product which has an overall H/C ratio of less than two, according to $$CH_3OH \rightarrow CH_{(2-2x)} + xH_2 + H_2O,$$

thereby forming more aromatics and less n- and i-paraffins, in particular, less light n- and i-paraffins, such as ethane, propane and butanes, and therefore providing improved gasoline yield and octane number.

The obtained hydrocarbon product of the present invention may be rich in aromatics and may be useful as a blendstock, e.g. similar to reformate, in refineries, or the product which may be upgraded by conventional means to provide a finished gasoline product.

Hydrogen Rejection

The dehydrogenation reaction, promoting the formation of aromatics, is equilibrium-limited and in a synthesis loop, hydrogen may build up until the dehydrogenation reaction becomes essentially extinct.

Therefore, removal of hydrogen from the loop ensures that the dehydrogenation reaction is sustained. The hydrogen removal may be continuous, carried out in intervals and/or determined by preselected or adapted desired $H_2$ concentrations e.g. in depleted or partially depleted recycle stream(s).

According to the invention $H_2$ may be at least partly removed by one or more methods removing $H_2$ at one or more stages, from one or more streams.

As mentioned above, removal of $H_2$ from the synthesis loop may be passive, i.e. by purging part of the gaseous recycle stream, or active, to be understood as methods by which one or more recycle streams are selectively depleted or partially depleted with respect to $H_2$.

Depending on the method used for $H_2$ removal more or less $H_2$ may be removed. Also, the selectivity in the removal towards $H_2$ may vary. For example if a permselective membrane is used for the removal the membrane may allow other substances than $H_2$ such as methane and carbon monoxide to pass through in which case not only $H_2$ is removed. Similarly e.g. oxidation steps may result in oxidation of other substances than $H_2$, e.g. carbon monoxide.

According to some embodiments an at least partially $H_2$ depleted recycle stream is obtained from the gaseous stream by passing the gaseous stream to a hydrogen permselective membrane. I.e. the gaseous stream is provided to a stage wherein the gas is passed to a membrane removing $H_2$. The permeation of $H_2$ in the selective membrane may be adjusted to leave a pre-determined amount of hydrogen in the retentate recycled to the conversion step as the at least partially $H_2$ depleted recycle stream.

Alternatively, the at least partially $H_2$ depleted recycle stream is obtained from the gaseous stream by passing said gaseous phase, after admixture with a predetermined amount of dioxygen, to a catalytic preferential oxidation, commonly known as PrOx, step where hydrogen is reacted with said predetermined amount of oxygen to form water and recycling said reacted stream, at least partially depleted in hydrogen, to the conversion step. The catalytic oxidation is preferably carried out at essentially the same pressure as in the conversion step. Catalysts effective in selective oxidation typically comprise a metal supported on an inorganic metal oxide.

Optionally, the at least partially $H_2$ depleted recycle stream is obtained from the gaseous stream by passing said gaseous phase, after admixture with a predetermined amount of a non-dioxygen hydrogen scavenger, to a catalytic oxidation step where hydrogen is reacted with said predetermined amount oxidizing agent and recycling said reacted stream, at least partly depleted in hydrogen, to the conversion step.

The hydrogen scavenger may be an aldehyde or a ketone, in which case said aldehyde and hydrogen is converted into an alcohol over a hydrogenation catalyst. For example, the aldehyde may be formaldehyde in which case formaldehyde and hydrogen is converted into methanol over a hydrogenation catalyst.

The hydrogen scavenger may be hydrogen peroxide in which case hydrogen peroxide and hydrogen is converted into water over a hydrogenation catalyst.

The hydrogen scavenger may be carbon oxides, CO and/or CO2 in which case carbon oxides are converted into methane over a methanation catalyst.

The separation step, where the effluent from the conversion step is separated into a gas phase and aqueous and hydrocarbon liquid phases, is typically conducted by cooling the conversion effluent essentially at the synthesis pressure, at 10-50 bar, typically by cooling to a temperature between 30 and 80° C. Under these conditions $H_2$ is almost only found in the gaseous phase in the separator, and the liquid hydrocarbon (as well as the aqueous phase) is almost completely $H_2$ free. This means that the liquid hydrocarbon phase may be separated into a product phase and one ox more lower- and/or higher-boiling phases, and at least one of the lower- and/or higher-boiling phases can then at least partially be recycled to the conversion step as one of one or more at least partially $H_2$ depleted recycle.

Thus, several embodiments according to the present invention are proposed, wherein hydrogen may be removed from the synthesis loop and thereby enhance the selectivity to aromatics. Other means of promoting the selectivity to aromatics for example includes increasing the temperature in the conversion reactor and/or reducing the pressure, thereby thermodynamically favouring the dehydrogenation reaction and, in turn, enhancing the selectivity to aromatics and reducing the selectivity to light paraffins.

The degree of $H_2$ removal affects the products from the conversion. As mentioned above, if no means of hydrogen removal is established, hydrogen will accumulate in the loop and, eventually, the dehydrogenation reaction will cease. Therefore, continuous removal of hydrogen from the loop may be required in order to sustain the dehydrogenation reaction. To which extent yield and selectivity may be increased depends on how much hydrogen is rejected from the synthesis loop. Thus, if only a limited part of the hydrogen is rejected, e.g. purging part of the recycle gas (passive rejection) this will lead to a product with a slight enrichment in aromatics, whereas a high degree of hydrogen rejection, as may be achieved by active $H_2$ rejection as described above, will provide a product with a high aromatics content and even with aromatics as the main constituent.

The extent of hydrogen removal, therefore, represents a convenient and efficient tool for controlling aromatics selectivity and product yield.

In a methanol-to-gasoline context removal of hydrogen, passive or active, will lead to a higher gasoline yield as well as improved octane due the enhanced selectivity to aromatics. In most areas the aromatics content is regulated, typically to 35 vol % (some 40 wt %), which imposes a limit to how much hydrogen may be removed. Nonetheless, a few percent improvement in gasoline yield and at the same time gaining a few numbers in octane represents a significant economic advantage. Moreover it may, be advantageous to operate a plant to exceed the aromatics selectivity beyond the limits regulations prescribe in order to provide a high-octane blendstock, e.g. for use in refineries. Additionally, as will be shown by examples, the selectivity to durene (1,2,4,5-tetramethylbenzene) and heavy oil (carbon number C11 and higher) is significantly reduced by the present process. I.e. the invention provides for making gasoline with improved yield and octane with reduced selectivity to durene and heavy oil.

The selectivity to aromatics increases with temperature, in part due to higher rates of reaction, but primarily, because dehydrogenation becomes favoured thermodynamically by an increase in temperature. Consequently, higher aromatic yields may be obtained by conducting the conversion at higher temperatures.

Thus the present process and plant provides a method for making hydrocarbons wherein the content of aromatics in the product slate may be controlled to a significant extent by applying a catalyst or a combination of catalysts active in dehydrogenation and methanol-to-hydrocarbons formation and a means of passive or active rejection of hydrogen from the synthesis loop, the degree of which passive and/or active, controls the amount of aromatics in the product slate.

The feed stream may e.g. comprise methanol, dimethyl ether or mixtures hereof.

In preferred embodiments the process is carried out in either a fixed bed or a fluid bed reactor.

The present invention also relates to a plant for the conversion of a feed stream comprising alcohols, ethers or mixtures (such as methanol) to hydrocarbons, said plant comprising
  means for supplying a feed stream comprising methanol,
  a conversion reactor
  a separator for separating a conversion effluent into a gaseous recycle stream, process condensate and a liquid product, and
  means for removing $H_2$ from the synthesis loop by purging part of the gaseous recycle stream, and/or by reducing the hydrogen concentration in at least part of the effluent thereby obtaining at least one at least partly $H_2$ depleted recycle stream.

As discussed above in relation to the process the plant may advantageously comprise means for removing $H_2$ from the recycle stream. The means for removing $H_2$ from the recycle stream may be, e.g., a selective membrane, a preferential oxidation (PrOx) and/or a step wherein a hydrogen scavenger is admixed into the recycle stream and reacted with hydrogen. Preferred scavengers comprise aldehydes, ketones, hydrogen peroxide or carbon oxides, reacting with hydrogen over a catalyst to form primary alcohols, secondary alcohols, water and/or methane, respectively.

I.e. the $H_2$ may be removed by various means. In the simplest way, $H_2$ may be removed by purging part of the gaseous recycle stream, thereby improving $C_{5+}$ yield, selectivity to aromatics and octane number. Further improvement may be achieved when hydrogen is actively rejected. When the desired product is aromatics, a simple purge may not be sufficient to provide an aromatics selectivity high enough to make such a process economically justifiable, even given the benefit of operating at higher temperature. Therefore, additional means of improving aromatics selectivity may be preferred involving active rejection of hydrogen from the synthesis loop by one or more of the methods described above.

Where a hydrogen scavenger such as formaldehyde is converted into methanol in the presence of $H_2$ and a hydrogenation catalyst the plant may further comprise a hydrogenation reactor wherein a hydrogen scavenger is converted into methanol in the presence of $H_2$ and a hydrogenation catalyst. The same applies to other hydrogen scavengers, such as hydrogen peroxide, converting into water by reaction with hydrogen. Also, excess hydrogen may be removed through methanation of CO and/or CO2.

Removal of hydrogen in gas streams by methanation and/or shift reaction is another method to create an at least partially H2 depleted recycle stream. A typical catalyst comprises nickel (Ni) supported on metal oxides (e.g. alumina). Steam (H2O) may be added as means of controlling the reaction.

A setup with a PrOx may provide the option of regulating the $H_2$ removal from 0-100%. In the PrOx reactor the $H_2$ removal may be controlled by controlling the $O_2$ flow rate to the PrOx reactor. A PrOx catalyst may typically consist of Pt, PtSn or In supported on an inorganic oxidic carrier.

Removal of hydrogen in gas streams by permselective membranes is a well-known technology, applied commercially and offered by a number of providers, e.g. Air Products, UOP and MTR Inc. Typically, the degree of hydrogen removal is determined by the pressure and the hydrogen concentration of the hydrogen-containing gas stream and the effective membrane area is determining for how much hydrogen can be removed. As mentioned above, other substances than $H_2$ such as methane and carbon monoxide will to some extent permeate the membrane.

Thus, where $H_2$ is removed from the gas stream from the separator the means for removing $H_2$ from at least part of the effluent obtaining at least one at least partly $H_2$ depleted recycle stream may be a selective membrane, a PrOx and/or a step wherein a hydrogen scavenger, typically formaldehyde, hydrogen peroxide or carbon oxides are converted into methanol, water or methane, respectively, in the presence of $H_2$ and a hydrogenation catalyst.

The means for removing $H_2$ from at least part of the effluent obtaining at least one at least partly $H_2$ depleted recycle stream may also, or alternatively, comprise means for separating the liquid hydrocarbon stream into at least a product phase and one or more lower- and/or higher-boiling phases and means for recycling at least one of said lower- and/or higher-boiling phases as the at least partly $H_2$ depleted recycle. Thus, the plant may comprise a second separator (or one or more additional separators) wherein the liquid hydrocarbon stream is separated into at least two fractions e.g. $C_3$-$C_4$ and a $C_5$ fraction. As the liquid hydrocarbon stream may contain $H_2$ to a very limited degree (as $H_2$ is present in gas phase in the first separator) at least part of the $C_3$-$C_4$ stream may be used a $H_2$ depleted recycle. From the second or one or more additional separators e.g. a light fraction comprising $H_2$ from the liquid hydrocarbon stream, $CH_4$, Co and/or $CO_2$ may also be obtained.

Catalysts

The catalysts applied in relation to this invention in general comprise an acidic component in the form of a micro porous catalyst, e.g. in the form of a zeolite (e.g. ZSM-5, ZSM-11 or ZSM-48) or a zeotype (e.g. a silicoaluminum phosphate) and a metal component/selected from the group of Zn, Ga, In, Ge, Ni, Ho, P, Ag, Sn, Pd and Pt. Also mixtures of two or more metals or metal Oxide may be applied, e.g., Pt—Sn, which is known as an efficient dehydrogenation catalyst.

Various methods may be applied to produce the catalyst: The two components may constitute an integrated entity, e.g. as obtained by introducing the metal component by impregnation or ion-exchange to the zeolite, either onto the zeolite itself or onto an extrudate in which the zeolite is embedded in a binder matrix, e.g. alumina. The metal component may also be added in the form of a salt or an oxide, together with binders or lubricants during fabrication of the acid component, e.g. during extrusion or pelletization.

Also physical mixtures of several acidic and metal components may be applied and the mixture may be charged to the reactor to form a uniform mixture or to form alternating layers or they may be graded to various degrees.

If the zeolite catalyst is a single bifunctional catalyst active towards both methanol to hydrocarbons and dehydrogenation, only one catalyst may be needed in the process.

In several embodiments of the present invention the acidic zeolite catalyst comprises metal and/or metal oxide in combination with a zeolite, e.g. H-ZSM-5.

The applicant has shown that, quite surprisingly, even at mild/moderate reaction conditions, such as applied in the conventional MTG process, a bifunctional catalyst comprising Zn and H-ZSM-5 i.e. a Zn/ZSM-5 catalyst shows significant selectivity to aromatics. The applicant also surprisingly found that using the incorporation of Zn into the acidic zeolite catalyst provided a hydrocarbon product with less durene. Durene (1,2,4,5-tetramethylbenzene) is a component that is formed in appreciable amounts in the methanol-to-gasoline process, typically in the range from 4-8 wt % in the gasoline product. Dye to its high melting point (79° C.) durene may cause plugging of the engine's fuel injection system in cold weather. Therefore, normal practice in synthetic gasoline manufacture involves a separate process step to reduce the amount of durene by hydroisomerization and dealkylation to provide a final gasoline with a durene content of less than about 4 wt % at which level durene has no negative impact on driveability. Therefore, reduced selectivity to durene is advantageous. The applicant also found that the zinc-containing catalyst showed a reduced selectivity to hydrocarbons with carbon numbers higher than C11, commonly referred to as heavy oil, which causes the end boiling point of the gasoline product to increase and, therefore, must be removed from the gasoline product in order to meet gasoline specifications, thereby representing a loss of gasoline product.

EXAMPLES

The following examples demonstrate the benefits of using a combination a Zn dopant and H-ZSM-5. It will be understood that the combination of H-ZSM-5 or other zeolites or zeo-types in combination with other metals or metal oxides capable of dehydrogenation of hydrocarbons may lead to similar effects as regards hydrocarbon yields and selectivities.

Catalyst Preparation

Catalysts applied in the examples were prepared by extrusion of H-ZSM-5 (CBV-8014 obtained from Zeolyst International and having a $SiO_2/Al_2O_3$ ratio of 80) with an alumina binder material in the proportion of 65 wt % of H-ZSM-5 and 35 wt % alumina binder, adding water to obtain a paste and extruding the paste through a die with a diameter of 1.4 mm. The extrudates were subsequently dried in air at 120° C. and calcined in air at 500° C. for four hours.

Samples of calcined extrudate were then impregnated with art aqueous solution of zinc nitrate: 40 g of extrudates was impregnated with a solution of 5.46 g $Zn\,(NO_3)_2$, $6H_2O$ in 25 ml of de-ionized water. The impregnated extrudates were dried overnight at 110° C. and finally calcined in air at 500° C. for 4 hours to obtain a catalyst containing 2.9 wt % Zn, A similar catalyst with a higher ziric loading of 9.6 wt % was prepared following the same procedure, but applying an impregnation solution of 20.7 g $Zn\,(NO_3)_2$, $6H_2O$ dissolved in 25 ml of de-ionized water.

Example 1-2

In a reference experiment (example 1) applying a typical MTG catalyst, a microreactor consisting of a 2 mm inner diameter isothermal reactor was charged with 0.10 g of H-ZSM-5 extrudates. The reactor was heated in an oven to 370° C. and pressurized to 20 bar g and the catalyst was contacted with a feed of 6.6 mol % methanol (balanced by nitrogen) at a weight hourly space velocity, WHSV (g methanol per g catalyst per hour) of 2.0.

In accordance with the present invention another experiment (example 2) was conducted under same conditions, using the same catalyst amount as above, but this time applying a Zn-impregnated catalyst containing 2.9 wt % zinc.

Results of the two experiments, averaging a test period of 30 hours are shown in Table 1.

TABLE 1

| Example | 1 | 2 |
|---|---|---|
| Temperature (° C.) | 370 | 370 |
| Pressure (bar g) | 20 | 20 |
| WHSV | 2.00 | 2.00 |
| Products (wt % of total HC) | | |
| n-paraffins | 17.64 | 11.27 |
| i-paraffins | 35.13 | 30.39 |
| Olefins | 8.51 | 15.55 |
| Naphthenes | 2.43 | 2.97 |
| Aromatics | 35.06 | 39.06 |
| C11+ ("heavy oil") | 0.89 | 0.50 |
| Propane & butanes | 31.84 | 20.62 |
| Overall molar H/C ratio in hydrocarbon product | 2.00 | 1.90 |
| Overall C5+ yield | 60.27 | 66.26 |
| Aromatics in C5+ fraction | 58.20 | 58.93 |
| Olefins in C5+ fraction | 3.38 | 5.49 |
| Durene in C5+ fraction | 8.36 | 6.51 |

By comparison, example 1 and 2 show that the Zn-containing catalyst provides a C5+ yield (wt % C5 of total hydrocarbon fraction) higher than the reference catalyst, a higher yield of aromatics and olefins, a reduced selectivity to C11+ ("heavy oil") and a reduced selectivity to durene. Also, the overall molar hydrogen-to-carbon (H/C) ratio of the hydrocarbon product is reduced when zinc is added to the catalyst, indicating that dehydrogenation (liberation as $H_2$) takes place over the catalyst, while the Zn-free catalyst provides a hydrocarbon product with a H/C ratio of 2.00, as expected from the mere dehydration of methanol.

Example 3

The experiment of example 2 was repeated, with the only difference that in this the catalyst impregnated with 9.6 wt % zinc was applied.

Results of the experiment, averaging a period of 30 hours are shown in Table 2 and compared with the result of example 2.

TABLE 2

| Example | 2 | 3 |
|---|---|---|
| Temperature (° C.) | 370 | 370 |
| Pressure (bar g) | 20 | 20 |

TABLE 2-continued

| Example | 2 | 3 |
|---|---|---|
| WHSV | 2.00 | 2.00 |
| Products (wt % of total HC) | | |
| n-paraffins | 11.27 | 9.10 |
| i-paraffins | 30.39 | 31.80 |
| Olefins | 15.55 | 13.47 |
| Naphthenes | 2.97 | 3.09 |
| Aromatics | 39.06 | 42.01 |
| C11+ ("heavy oil") | 0.50 | 0.32 |
| Propane & butanes | 20.62 | 17.94 |
| Overall molar H/C ratio in hydrocarbon product | 1.90 | 1.87 |
| Overall C5+ yield | 66.26 | 70.69 |
| Aromatics in C5+ fraction | 58.93 | 59.44 |
| Olefins in C5+ fraction | 5.49 | 4.89 |
| Durene in C5+ fraction | 6.51 | 6.98 |

Example 3 demonstrates that the incorporation of additional zinc leads to a further increase in the yield of aromatics and C5+ hydrocarbons and a further reduction in the selectivity to "heavy oil". Incorporation of additional Zn to the catalyst is also reflected by a further decrease in the H/C ratio.

Example 4

Examples 1-3 demonstrate that incorporation of Zn onto the catalyst provides higher aromatic yield and higher C5+ yield, whereas the amount of aromatics in the C5+ fraction remains essentially constant. This following example shows the effect of increasing the temperature in the reactor: The experiment of example 3 was repeated using the same catalyst, except that the temperature was increased to 420° C.

Results of this experiments averaging a period of 30 hours are reported in Table 3 and compared with the result of example 3.

TABLE 3

| Example | 3 | 4 |
|---|---|---|
| Temperature (° C.) | 370 | 420 |
| Pressure (bar g) | 20 | 20 |
| WHSV | 2.00 | 2.00 |
| Products (wt % of total HC) | | |
| n-paraffins | 9.10 | 13.62 |
| i-paraffins | 31.80 | 20.32 |
| Olefins | 13.47 | 8.11 |
| Naphthenes | 3.09 | 1.73 |
| Aromatics | 42.01 | 55.92 |
| C11+ ("heavy oil") | 0.32 | 0.63 |
| Propane & butanes | 17.94 | 18.59 |
| Overall molar H/C ratio in hydrocarbon product | 1.87 | 1.76 |
| Overall C5+ yield | 70.69 | 70.66 |
| Aromatics in C5+ fraction | 59.44 | 79.12 |
| Olefins in C5+ fraction | 4.89 | 1.39 |
| Durene in C5+ fraction | 6.98 | 1.65 |

Example 4 demonstrates that, by increasing the temperature, the selectivity towards aromatics is significantly enhanced, from about 42 wt % to about 56 wt % of the total hydrocarbon fraction, and the C5 fraction becomes substantially richer in aromatics. Also the amount of heavier aromatics, such as durene, is significantly reduced and the overall H/C ratio is significantly reduced as well.

Examples 5-7

Examples 5-7 demonstrate the influence of hydrogen on yield and selectivity. A reference experiment with un-doped H-ZSM-5 (example 5) was conducted at 420° C. and a weight hourly space velocity of 1.6. Example 5 was then repeated, except that the same Zn-doped catalyst as applied in example 2 was applied (example 6). Finally, example 6 was repeated, but this time the nitrogen carrier gas was replaced by a mixture of 5 vol % hydrogen in nitrogen (example 7).

The results of the three experiments, averaging a period of 30 hours are reported in Table 4.

TABLE 4

| Example | 5 | 6 | 7 |
|---|---|---|---|
| Temperature (° C.) | 420 | 420 | 420 |
| Pressure (bar g) | 20 | 20 | 20 |
| WHSV | 1.6 | 1.6 | 1.6 |
| Carrier gas (vol % $H_2/N_2$) | 0/100 | 0/100 | 5/95 |
| Average over period (hrs) | 0-30 | 0-30 | 0-30 |
| Products (wt % of total HC) | | | |
| n-paraffins | 27.30 | 12.45 | 14.31 |
| i-paraffins | 27.86 | 24.52 | 29.89 |
| Olefins | 7.92 | 13.79 | 9.04 |
| Naphthenes | 1.30 | 2.56 | 2.94 |
| Aromatics | 35.18 | 46.50 | 43.72 |
| C11+ ("heavy oil") | 0.61 | 0.58 | 0.38 |
| Propane & butanes | 39.33 | 19.11 | 23.20 |
| Overall molar H/C ratio in hydrocarbon product | 2.01 | 1.83 | 1.89 |
| Overall C5+ yield | 50.50 | 66.99 | 65.98 |
| Aromatics in C5+ fraction | 69.91 | 69.38 | 66.25 |
| Olefins in C5+ fraction | 1.76 | 3.76 | 2.11 |
| Durene in C5+ fraction | 1.48 | 2.54 | 1.96 |

By comparing example 6 with reference example 5 it is again shown that incorporation of Zn to the H-ZSM-5 catalyst leads to a significant improvement in yield and aromatics selectivity. The effect of hydrogen at the inlet of the reactor is demonstrated by comparing example 6 and 7, showing that the presence of hydrogen causes a decline in the aromatics selectivity and a slight reduction in the $C_{5+}$ yield. However, when comparing example 7 with reference example 5 it is clear that, despite the presence of hydrogen, the $C_{5+}$ yield and aromatics selectivity is still significantly higher, showing that the Zn-doped catalyst is capable of improving yield and aromatics selectivity even when hydrogen is present at the reactor inlet. This demonstrates that, in a synthesis loop, controlling the amount of hydrogen recycled to the conversion reactor inlet provides a means of directing the selectivity towards aromatics.

It is also observed (example 6 & 7) that the presence of hydrogen reduces the formation of durene and heavy oil. At the high temperatures applied in examples 5-7 some increase in durene levels are observed when applying the Zn-doped catalysts relative to the un-doped catalyst. However, in these examples durene selectivity are already so low (below 4 wt %) that it is without any significance to driveability.

In conclusion, examples 5-7 show that the incorporation of Zn to the zeolite increases the aromatics selectivity and the $C_{5+}$ yield, even so in the presence of hydrogen in the feed and that the presence of hydrogen in the feed leads to a reduction in the formation of durene and heavy oil. Thus, in a synthesis loop, finite amounts of hydrogen in the recycle stream is not necessarily prohibitive in regard to achieving the desired effects according to the present invention, namely that of increasing $C_{5+}$ yield and aromatics.

In the following the process and plant is further described with reference to the accompanying drawings. The drawings show exemplary embodiments of the present process and plant and are not to be construed as limiting to the scope of the present application.

Figure 1:
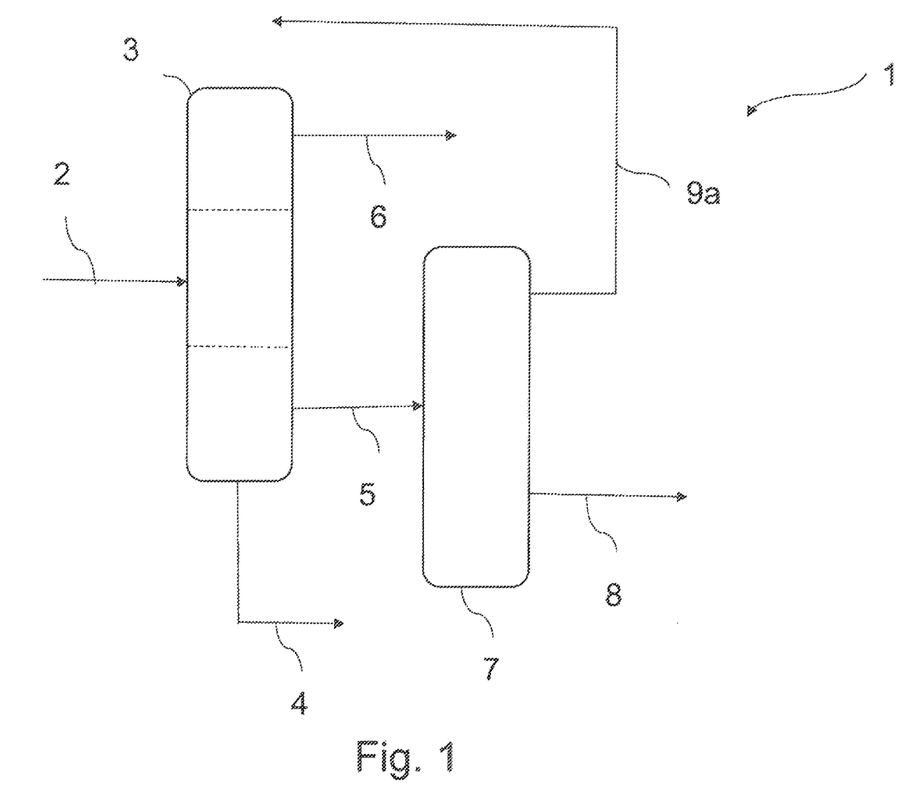
FIG. 1 shows a schematic setup of a first embodiment according to the present invention.

FIG. 1 shows a schematic overview 1 of a plant/process according to the present application. A conversion effluent 2 is fed to a first separator 3 wherein the conversion effluent is separated into three streams: process condensate 4, first product stream (liquid Hydrocarbon stream) 5 and a gas stream 6.

The first product stream is fed to a second separator 7 wherein the first product stream is separated into a second product stream (product phase) 8 and a LPG stream comprising C3-C4 wherefrom the recycle stream 9a is taken.

As described herein the first product stream is near $H_2$ free and $H_2$ is present predominantly in the gas phase in the first separator. Thus when the first product stream is separated into the second product stream 8 and the recycle stream the recycle stream obtained is a $H_2$ depleted recycle.

The second product stream 8 may be send to further processing, upgrade, storage etc.

Figure 2:
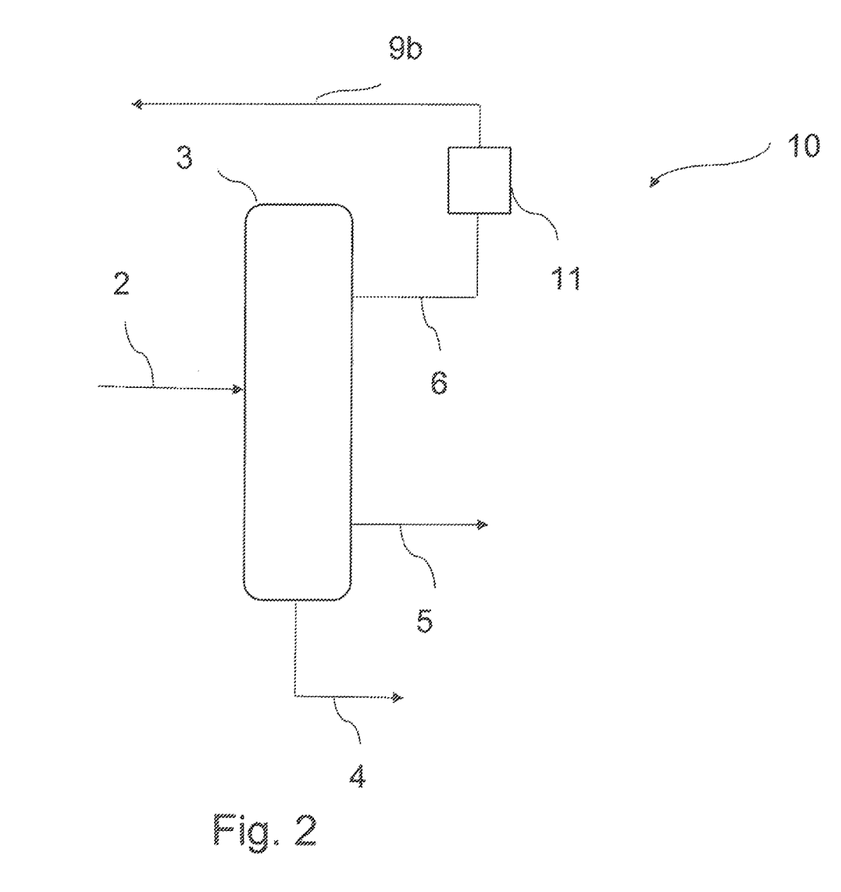
FIG. 2 shows a schematic setup of a second embodiment according to the present invention.

FIG. 2 shows a schematic overview 10 of a plant/process according to the present application. A conversion effluent 2 is fed to a first separator 3 wherein the conversion effluent is separated into three streams: process condensate 4, first product stream 5 and a gas stream 6. At least part of the gas stream 6 is taken through a $H_2$ depletion step 11 whereby a $H_2$ depleted recycle stream 9b obtained.

The $H_2$ depletion step 11 may comprise e.g. a $H_2$ permeable membrane and/or a catalytic oxidation step.

Figure 3:
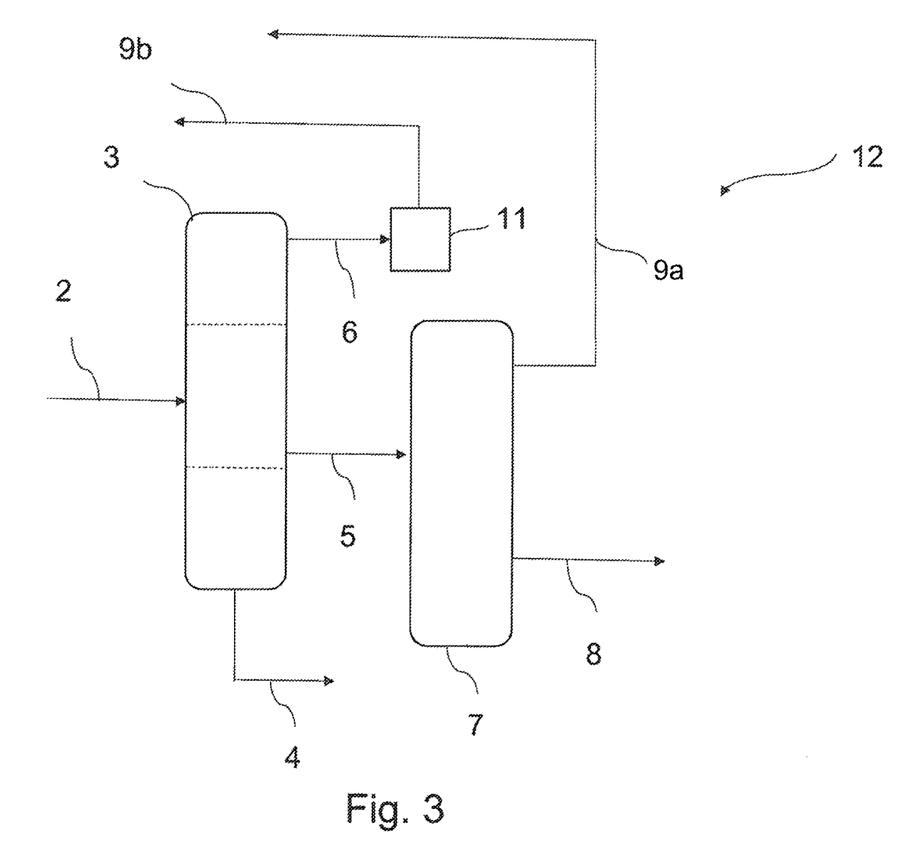
FIG. 3 shows a schematic setup of third embodiment according to the present invention.

FIG. 3 shows a schematic overview 12 of a plant/process wherein the embodiments of FIGS. 1 and 2 are combined whereby a $H_2$ depleted stream is obtained from the gas stream 9b and from the LPG fraction taken from the second separator as $H_2$ depleted stream 9a.

In the embodiments of FIGS. 1, 2 and 3 the one or more H2 depleted streams are returned to the conversion step (not shown) from which the conversion effluent 2 is obtained. The conversion step may be a MTG or a MTA process.

Figure 4:
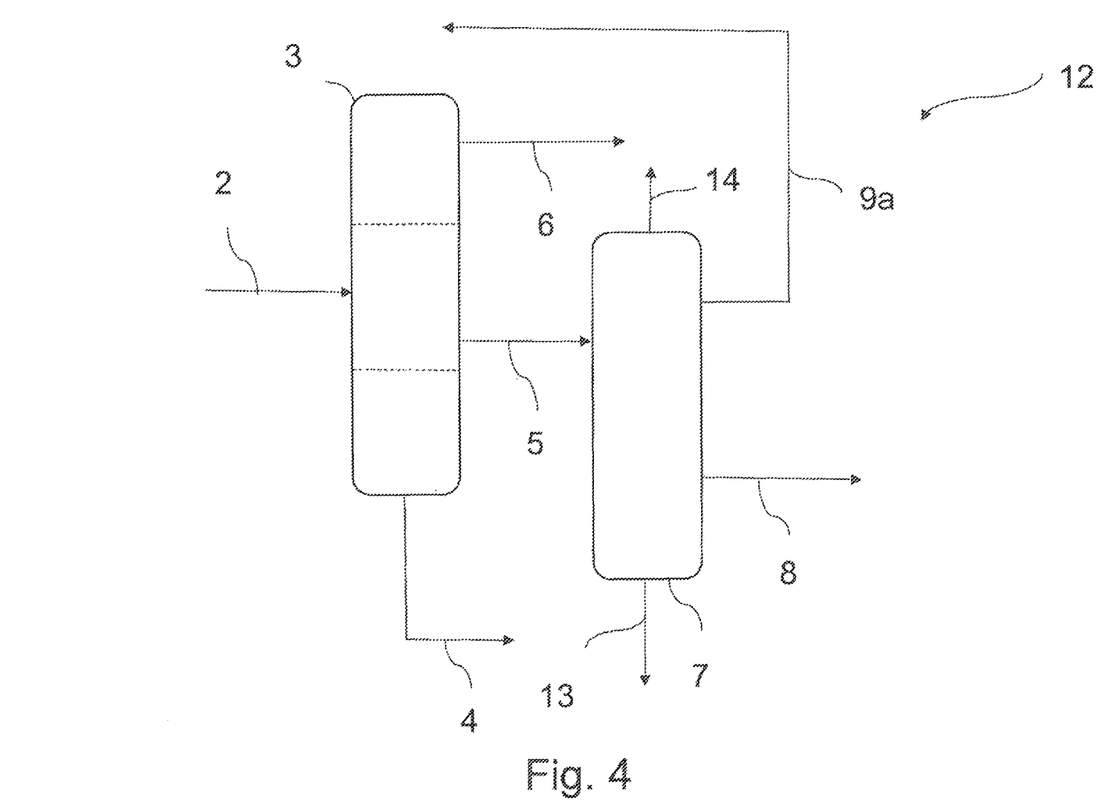
FIG. 4 shows a schematic MTG setup according to the present invention.

FIG. 4 shows a schematic overview 12 of a MTG plant/process according to the present application. A conversion effluent 2 is fed to a first separator 3 wherein the conversion effluent is separated into three streams: process condensate 4, first product stream (liquid hydrocarbon stream) 5 and a gas stream 6. Here the liquid hydrocarbon stream is raw gasoline as the process is MTG.

The raw gasoline is fed to one or more separators 7 here illustrated by a single separator. In the one or more separator steps the first product stream/raw gasoline is separated into a second product stream which in this case may be gasoline or stabilized gasoline 8 and a LPG stream comprising C3-C4 wherefrom the at least partly $H_2$ depleted recycle stream 9a is taken. From the one or more separation steps 7 one or more additional streams may be obtained including a heavy oil stream 13 containing products with higher boiling point than final boiling point specs for the gasoline.

The raw gasoline 5 contains only little $H_2$ as $H_2$ is present predominantly in the gas phase in the first separator. Thus when the first product stream is separated into the second product stream 8 and the recycle stream, the recycle stream obtained is a $H_2$ depleted recycle. Any $H_2$ present in the raw gasoline may be removed as part of a light fraction stream 14 further comprising e.g. $CH_4$, CO and $CO_2$.

The second product stream 8 may be send to further processing, upgrade, storage etc.

The invention claimed is:

1. A process for production of a hydrocarbon product suitable for use as gasoline or as a blendstock, said process comprising:
    converting a feed stream comprising alcohols, ethers or mixtures thereof over a metal-containing zeolite based catalyst, active in dehydrogenation of hydrocarbons, in a conversion step thereby obtaining a conversion effluent,
    separating said effluent to obtain an aqueous process condensate stream, a liquid hydrocarbon stream and a gaseous stream,
    removing $H_2$ from at least part of the effluent thereby obtaining at least one at least partially $H_2$ depleted recycle stream, wherein removing $H_2$ is via a selective membrane, a selective oxidation step and/or a step wherein a hydrogen scavenger is converted into methanol or water in the presence of $H_2$ and a hydrogenation catalyst, and
    recycling the at least one at least partially $H_2$ depleted recycle stream to the conversion step.

2. The process according to claim 1, wherein at least part of the gaseous phase is recycled to the conversion step.

3. The process according to claim 1, wherein the conversion step takes place in two or more consecutive reactors.

4. The process according to claim 1, wherein the at least part of the recycle stream or recycle streams is returned to one or more points upstream the conversion step.

5. The process according to claim 1, comprising a step regulating the $H_2$ content in the at least partly $H_2$ depleted recycle stream.

6. The process according to claim 1, wherein the zeolite based catalyst is a single bifunctional catalyst catalysing both methanol to hydrocarbons and dehydrogenation.

7. The process according to claim 1, wherein the zeolite based catalyst comprises a mixture of two or more catalysts which in combination catalyse both methanol to hydrocarbons and dehydrogenation reactions.

8. The process according to claim 1, wherein the zeolite based catalyst comprises a metal and/or metal oxide and a zeolite.

9. The process according to claim 1, wherein catalyst comprises a zeolite and a metal selected from the group consisting of Zn, Ga, In, Mo, Ag, P, Ge, Sn, Pd and Pt.

10. The process according to claim 1, wherein the process is carried out in one or more fixed bed reactors.

11. The process according to claim 1, wherein the process is carried out in one or more fluid bed reactors.

12. The process according to claim 1, wherein the dehydrogenation catalyst is arranged as a top and/or bottom layer in the conversion reactor and/or in one or more separate dehydrogenation reactors.

13. A plant comprising:
    means for supplying a feed stream comprising methanol, dimethyl ether or mixtures thereof
    a conversion reactor
    a separator for separating a conversion effluent into a gaseous recycle stream, process condensate and a liquid product, means for removing $H_2$ from at least part of the effluent thereby obtaining at least one at least partially $H_2$ depleted recycle stream, and means for recycling the at least partially $H_2$ depleted recycle stream, wherein the means for removing $H_2$ from at least part of the effluent obtaining at least one at least partly $H_2$ depleted recycle stream is a selective membrane, a selective oxidation step and/or a step wherein a hydrogen scavenger is converted into methanol or water in the presence of $H_2$ and a hydrogenation catalyst.

14. A plant comprising:

means for supplying a feed stream comprising methanol, dimethyl ether or mixtures thereof a conversion reactor a separator for separating a conversion effluent into a gaseous recycle stream, process condensate and a liquid product, means for removing $H_2$ from at least part of the effluent thereby obtaining at least one at least partially $H_2$ depleted recycle stream, and means for recycling the at least partially $H_2$ depleted recycle stream, wherein the means for removing $H_2$ from at least part of the effluent obtaining at least one at least partly $H_2$ depleted recycle stream comprises means for separating the liquid hydrocarbon stream into at least a product phase and one or more lower- and/or higher-boiling phases and means for recycling at least one of said lower- and/or higher-boiling phases as the at least partly $H_2$ depleted recycle stream.

15. Product obtained by the process according to claim 1.

16. Gasoline obtained by the process according to claim 1.

17. Reformate blendstock obtained by the process according to claim 1.

18. High octane gasoline blendstock obtained by the process according to claim 1.

19. A process for production of a hydrocarbon product suitable for use as gasoline or as a blendstock, said process comprising:

converting a feed stream comprising alcohols, ethers or mixtures thereof over a metal-containing zeolite based catalyst, active in dehydrogenation of hydrocarbons, in a conversion step thereby obtaining a conversion effluent, separating said effluent to obtain an aqueous process condensate stream, a liquid hydrocarbon stream and a gaseous stream, removing $H_2$ from at least part of the effluent thereby obtaining at least one at least partially $H_2$ depleted recycle stream, wherein removing $H_2$ is via separating the liquid hydrocarbon stream into at least a product phase and one or more lower- and/or higher-boiling phases and recycling at least one of said lower- and/or higher-boiling phases as the at least partly $H_2$ depleted recycle, and recycling the at least one at least partially $H_2$ depleted recycle stream to the conversion step.

20. The process according to claim 19, wherein the feed stream comprises methanol, dimethyl ether or mixtures thereof.

21. The process according to claim 19, wherein the liquid hydrocarbon stream and/or product phase comprises raw gasoline, stabilized gasoline or gasoline with an aromatics content below 40%, a hydrocarbon product suitable as blend stock.

22. The process according to claim 19, wherein the liquid hydrocarbon stream and/or product phase has a durene content below 6%.

23. The process according to claim 19, wherein the hydrocarbon product is a high octane gasoline blendstock.

24. The plant of claim 13, wherein the means for removing $H_2$ from at least part of the effluent obtaining at least one at least partly $H_2$ depleted recycle stream is a selective membrane.

25. The plant of claim 13, wherein the means for removing $H_2$ from at least part of the effluent obtaining at least one at least partly $H_2$ depleted recycle stream is a selective oxidation step.

26. The plant of claim 13, wherein the means for removing $H_2$ from at least part of the effluent obtaining at least one at least partly $H_2$ depleted recycle stream is a step wherein a hydrogen scavenger is converted into methanol or water in the presence of $H_2$ and a hydrogenation catalyst.

27. The process according to claim 1, wherein the feed stream comprises methanol, dimethyl ether or mixtures thereof.

28. The process of claim 1, wherein removing $H_2$ is via a selective membrane.

29. The process of claim 1, wherein removing $H_2$ is via a selective oxidation step.

30. The process of claim 1, wherein removing $H_2$ is via a step wherein a hydrogen scavenger is converted into methanol or water in the presence of $H_2$ and a hydrogenation catalyst.

* * * * *